(12) United States Patent
Ho et al.

(10) Patent No.: US 8,530,700 B2
(45) Date of Patent: Sep. 10, 2013

(54) PROCESS FOR PRODUCING ACRYLIC ACID

(75) Inventors: Fungau Ho, Charleston, WV (US); Olan S. Fruchey, Hurricane, WV (US); Roger L. Roundy, Rosharon, TX (US); William G. Etzkorn, Hurricane, WV (US); Christopher T. Reeves, Durham, NC (US); Mahmood Jawaid, Cross Lanes, WV (US); Edmund J. Yang, Houston, TX (US); Dennis W. Jewell, Angleton, TX (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 13/469,215

(22) Filed: May 11, 2012

(65) Prior Publication Data

US 2012/0226074 A1 Sep. 6, 2012

Related U.S. Application Data

(62) Division of application No. 12/439,620, filed as application No. PCT/US2007/077369 on Aug. 31, 2007, now Pat. No. 8,242,308.

(60) Provisional application No. 60/844,876, filed on Sep. 15, 2006.

(51) Int. Cl.
*C07C 51/42* (2006.01)
*C07C 51/16* (2006.01)

(52) U.S. Cl.
USPC .......................................... 562/600; 562/545

(58) Field of Classification Search
None
See application file for complete search history.

(56) References Cited

U.S. PATENT DOCUMENTS

| | | | |
|---|---|---|---|
| 5,817,865 A | 10/1998 | Machhammer et al. | |
| 5,910,607 A * | 6/1999 | Sakakura et al. | 562/532 |
| 6,294,056 B1 | 9/2001 | Matsumoto et al. | |
| 6,409,886 B1 | 6/2002 | Matsumoto et al. | |
| 6,448,439 B1 | 9/2002 | Eck et al. | |
| 6,498,272 B1 | 12/2002 | Schroder et al. | |
| 6,525,216 B1 | 2/2003 | Nishimura et al. | |
| 6,541,652 B2 | 4/2003 | Prinz et al. | |
| 6,555,707 B1 | 4/2003 | Nestier et al. | |
| 6,646,161 B1 | 11/2003 | Eck et al. | |
| 6,677,482 B2 | 1/2004 | Nishimura et al. | |
| 6,679,939 B1 | 1/2004 | Thiel et al. | |
| 6,727,383 B1 | 4/2004 | Nestler et al. | |
| 6,787,001 B2 | 9/2004 | Sakamoto et al. | |
| 6,939,991 B2 | 9/2005 | Thiel et al. | |
| 7,150,809 B2 | 12/2006 | Diehl et al. | |
| 7,151,194 B2 | 12/2006 | Ueno et al. | |
| 7,319,169 B2 | 1/2008 | Kang et al. | |
| 7,321,060 B2 * | 1/2008 | Serata et al. | 562/600 |
| 7,332,626 B2 | 2/2008 | Hirao et al. | |
| 7,511,172 B2 * | 3/2009 | Hirao et al. | 562/532 |
| 7,632,968 B2 | 12/2009 | Kang et al. | |
| 7,786,323 B2 | 8/2010 | Yada et al. | |

(Continued)

FOREIGN PATENT DOCUMENTS

WO   WO 99/50222   10/1999

*Primary Examiner* — Karl J Puttlitz

(74) *Attorney, Agent, or Firm* — Lynn B. Morreale

(57) ABSTRACT

The process for the distillation of a gas mixture comprising (meth)acrylic acid obtained from the gas-phase oxidation of at least one (meth)acrylic acid precursors is improved through the use of coupled distillation columns. In a first column, the gaseous mixture is dehydrated while in a second column, the dehydrated gaseous mixture is distilled into product, overhead and bottoms streams.

20 Claims, 5 Drawing Sheets

(56) References Cited

U.S. PATENT DOCUMENTS

| | | |
|---|---|---|
| 2001/0021788 A1 | 9/2001 | Matsumoto et al. |
| 2004/0046270 A1 | 3/2004 | Diehl et al. |
| 2004/0220427 A1 | 11/2004 | Yada et al. |
| 2004/0225152 A1* | 11/2004 | Yada et al. .................. 562/600 |
| 2004/0249199 A1 | 12/2004 | Ueno et al. |
| 2004/0249200 A1* | 12/2004 | Serata et al. ................ 562/545 |
| 2004/0249201 A1 | 12/2004 | Ueno et al. |
| 2005/0171380 A1 | 8/2005 | Bub et al. |

* cited by examiner

PROCESS FOR PRODUCING ACRYLIC ACID

CROSS-REFERENCE TO RELATED APPLICATION

This application is divisional application of U.S. patent application Ser. No. 12/439,620, filed Mar. 2, 2009 which is a national stage application under 35 U.S.C, §371 of PCT/US2007/77369, filed Aug. 31, 2007 which claims benefit to U.S. Application No. 60/844,876 filed on Sep. 15, 2006 all of which are hereby incorporated by reference.

BACKGROUND OF THE INVENTION

Acrylic acid and the commodity acrylate esters (methyl, ethyl, butyl, and 2-ethylhexyl) comprise one of the most versatile monomer series for controlling polymer performance characteristics. These monomers all have an alpha beta unsaturated carboxyl structure and find extensive applications in surface coatings, adhesives and plastics. Furthermore, the sodium salt of polyacrylic acid is widely used as the superabsorbent polymer found in baby diapers. World production capacity for crude acrylic acid is almost eight billion pounds per year.

The first synthesis of acrylic acid was reported in 1843. This was accomplished via air oxidation of acrolein. Acrylic acid, a mature commodity chemical, has been well reviewed in the literature and has been commercially available since 1927. It has been manufactured on a commercial scale using several different technologies and raw materials, including the following:

1) Ethylene cyanohydrin process. The original version of this process reacted ethylene chlorohydrin with sodium cyanide to make ethylene cyanohydrin. A later modification reacted ethylene oxide with hydrogen cyanide. In both cases the ethylene cyanohydrin was treated with 85% sulfuric acid to yield acrylic acid and the by-product ammonium hydrogen sulfate.
2) Acetylene (Reppe) Process. The original or stoichiometeric version of this process reacted acetylene with nickel carbonyl and hydrochloric acid yielding acrylic acid, hydrogen gas and nickel chloride. A later version of the process used a nickel bromide/copper (II) bromide catalyst and reacted acetylene with carbon monoxide and water yielding acrylic acid.
3) Beta-Propiolactone Process. Ketene was reacted with formaldehyde in the presence of an aluminum chloride catalyst to obtain beta-propiolactone which was then treated with aqueous sulfuric or phosphoric acid, giving acrylic acid.
4) Acrylonitrile hydrolysis. Acrylonitrile is readily hydrolyzed with 85% sulfuric acid yielding acrylic acid and ammonium hydrogen sulfate by-product.

All of these technologies have been replaced in commercial practice by the currently employed high temperature, vapor phase, two stage air oxidation of propylene process. The development of highly active and very selective heterogeneous catalysts was the key to the technology. In the first stage propylene is oxidized with air to acrolein and then fed directly to the second stage where the acrolein is further oxidized with air to acrylic acid. The catalysts used in the two stages are mixed metal oxides that have been optimized for their respective chemistries. The first stage catalyst is composed of mainly molybdenum and bismuth oxides with several other metals. The second stage catalyst is also a complex mixed metal oxide catalyst where the oxides employed are primarily of molybdenum and vanadium. Several other components have been incorporated in the catalyst to optimize activity and selectivity. Acrylic acid yields of 80-90% from propylene have been realized for these commercial catalyst systems.

The feed gas to the acrylic acid reactors is typically 6-9 vol % propylene and 12-15 vol % oxygen (coming from air) with a make up of either recycle gas or low pressure steam. The steam (or recycle gas) is added as a diluent to avoid forming a flammable mixture of propylene and oxygen. Typically the mixture is kept on the fuel rich side of the flammable envelope. A stoichiometric excess of oxygen is normally fed to the reactors to prevent reduction of the catalyst. The oxygen to propylene molar ratio is generally held between 1.6 and 2.0, which means that the exit gases contain oxygen.

The original acrylic acid processes used water as the diluent, which meant that the reactor product yielded an approximately 35% aqueous acrylic acid solution upon quenching and separation of the noncondensible gases in the quench or absorber tower. This low concentration of acrylic acid in water had to be recovered via a solvent based extraction followed by several distillation steps to generate a technical grade acrylic acid. Technical grade acrylic acid is used to prepare the higher purity glacial acrylic acid or to prepare acrylates, i.e. esters of acrylic acid. When recycle gas technology was introduced, the aqueous acrylic acid obtained in the quench tower was concentrated to approximately 65% which allowed the use of solvent based azeotropic distillation to remove the water. The crude acrylic acid after water removal was then subjected to several distillation steps to yield a technical grade acrylic acid. An alternate technology for recovery of the 65% aqueous acrylic acid involves the introduction of a high boiling solvent in the quench tower to absorb the acrylic acid via a solvent swap. The base of the quench tower yields acrylic acid dissolved in this high boiling solvent instead of water. The acrylic acid is then subjected to further distillation steps for recovery from the high boiling solvent to yield technical grade acrylic acid.

The problem associated with all these recovery systems is the high capital and operation costs associated with the purification towers. Each tower requires the addition of fresh inhibitor at the top of the tower to prevent polymer fouling. The inhibitor is very expensive and adds to the production cost of acrylic acid. Furthermore, these systems all require use of a solvent which adds cost and environmental concerns. It would be desirable to have an acrylic acid recovery system with reduced capital and operation costs.

SUMMARY OF THE INVENTION

The present invention is such a recovery system, applicable to acrylic acid as well as methacrylic acid, which comprises a solvent-free distillation system requiring no more than two towers for generation of technical grade acrylic acid.

In one embodiment, the invention is a process comprising:

A. Cooling a gaseous reaction mixture comprising (meth)acrylic acid, the mixture obtained from the gas-phase oxidation of at least one (meth)acrylic acid precursor;

B. Dehydrating the cooled gas mixture in a dehydration column to produce an overhead stream and a bottoms stream; and C. At least partially condensing the overhead stream to form a condensate, and returning at least a portion of the condensate to the dehydration column as reflux.

In another embodiment, the invention is a process comprising:

A. Cooling a gaseous reaction mixture comprising (meth)acrylic acid, the mixture obtained from the gas-phase oxidation of at least one (meth)acrylic acid precursor;

B. Dehydrating the cooled gas mixture in a dehydration column to produce a dehydration column overhead stream and a dehydration column bottoms stream;

C. At least partially condensing the dehydration column overhead stream to form a condensate, and returning at least a portion of the condensate to the dehydration column as reflux;

D. Dividing the dehydration column bottoms stream into at least first and second dehydration column bottom streams, and passing at least a portion of one of the first and second dehydration column bottoms stream to a dehydration column heater/reboiler and passing at least a portion of the other dehydration column bottoms stream to the upper half of a second column, preferably to the top of the second column;

E. Subjecting the portion of the bottoms stream passed to the second column to distillation within the second column to produce at least a second column overhead stream and a second column bottoms stream comprising heavy components;

F. At least partially condensing the second column overhead stream to form a second overhead condensate, and passing at least a portion of the second overhead condensate to the dehydration column heater/reboiler; and G. Passing at least a portion of the second column bottoms stream to a second column heater/reboiler.

In one embodiment, a side draw product stream is recovered from the second column either as a liquid or vapor. In the case of a liquid side stream, the product is taken as a liquid draw from a tray (e.g. a hat tray). This liquid will contain the high boiling impurities, e.g., heavy components, that are present on the tray. In the case of a vapor side stream, the product is obtained by removing vapor from the tray and condensing it. The condensed liquid will have much lower levels of the high boiling impurities than the levels found in the liquid side stream product.

In one embodiment, the gaseous reaction mixture is primarily, if not exclusively, cooled within the dehydration column while in another embodiment, it is at least primarily cooled in a separate, direct contact device, e.g., a spray cooler or mixing device, prior to entering the dehydration column. In its simplest form, this direct contact device can be a section of the piping that conveys the hot, gaseous reaction mixture to the dehydration column. In still another embodiment, the bottoms stream from the dehydration column first passes through at least one cooler and a surge tank before entering the second column. In yet another embodiment, at least part of the dehydration column is constructed of a copper-containing metal to assist in the abatement of fouling.

The invention also includes a process for distillation of a gas mixture containing methacrylic acid or acrylic acid, the gas mixture being obtained from the gas-phase oxidation of (meth)acrylic acid precursors, the improvement comprising employing coupled distillation columns.

Surprisingly, the process of the invention can produce technical grade acrylic acid using no more than two distillation columns. The fact that only 2 columns are required results in lower capital expenditures and reduced operating costs. Advantageously, the process of the invention does not require a solvent, which also leads to reduced operational costs.

DETAILED DESCRIPTION OF THE INVENTION

Figure 1:
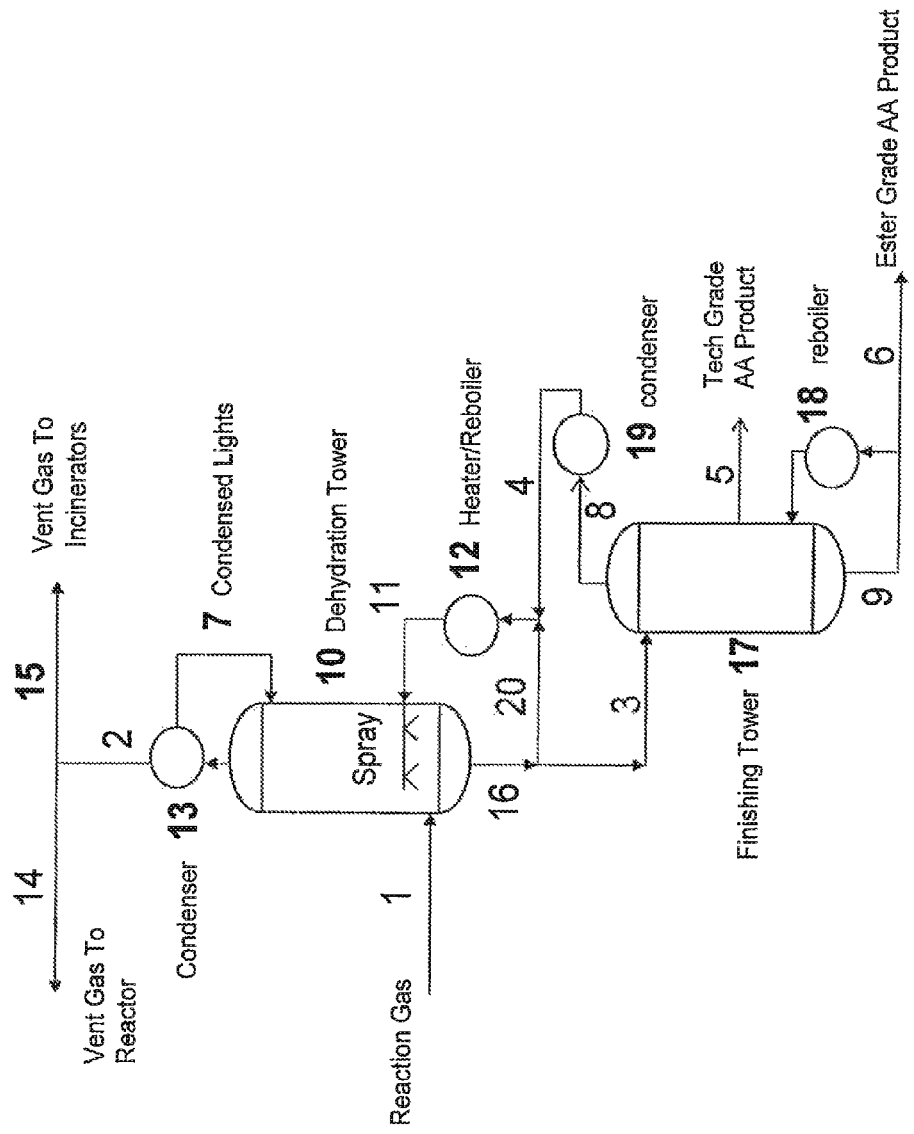
FIG. 1 is a schematic process flow sheet showing a configuration in which cooling of the reaction mixture is conducted primarily in the dehydration column.

The numerical ranges in this disclosure include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, temperature, pressure, equipment sizes, relative amounts of components in mixtures and/or blends, and the like.

The term "(meth)" indicates that the methyl substituted compound is included in the term. For example, the term (meth)acrylic acid represents acrylic acid and methacrylic acid. While the process of the present invention can be employed in the production of acrylic acid and methacrylic acid, for the sake of simplicity the following description will refer to acrylic acid.

For the purposes of the invention, the terms "light" and "light compound" and their plurals refer to a compound or compounds having a boiling point or boiling points below the boiling point of the desired product. For example, water is an example of a light compound when the desired product is acrylic acid. A lights stream contains at least one light compound.

Similarly, the term "heavies" for the purposes of the invention means compounds having a boiling point above the boiling point of the desired product. Oligomers of acrylic acid and well known Michael addition products are examples of heavies when the desired product is acrylic acid.

The term "separation system" refers to the equipment comprising a dehydration column and a second column, as are described herein, used in the process of the invention.

The term "technical grade acrylic acid" refers to an acrylic acid that contains at least 98.5% acrylic acid by weight, preferably contains at least 99% acrylic acid, and more preferably at least 99.5% acrylic acid. Furthermore the acrylic acid contains less than 0.5% water and less than 0.4% acetic acid, preferably contains less than 0.3% water and less than 0.2% acetic acid, and more preferably contains less than 0.15% water and less than 0.075% acetic acid.

The term "coupled distillation columns" refers to two distillation columns connected in a manner such that the tails stream from the first column is fed directly or indirectly into the top of the second column while the overhead stream of the second column is fed directly or indirectly into the base of the first column. "Indirectly" means that the stream first passes through at least one other vessel, e.g., a surge tank and/or heat exchanger, before entering the first or second column.

The feed stream to the process of the invention preferably is a gaseous reaction mixture. Preferably, this mixture results from the two-step catalytic vapor phase oxidation of at least one (meth)acrylic acid precursor, such as propylene in the case of acrylic acid or isobutylene in the case of methacrylic acid. The second step of the oxidation process typically converts an intermediate, such as (meth)acrolein, to the final product. This well-known oxidation process is widely used commercially. See U.S. Pat. No. 6,646,161 B1, the teachings of which are incorporated herein by reference, for a discussion the composition of the hot gaseous reaction mixture.

The first step of the process of the invention is to cool the gaseous reaction mixture. The gaseous reaction mixture typically is superheated as it comes from the reactor system, in other words, it contains more heat (energy) than the amount of heat required to vaporize the mixture. In one embodiment of the invention, the cooling step removes essentially all of the amount of superheat from the gaseous reaction mixture. For example, the hot acrylic acid reactor outlet gases and vapors are cooled to less than 260 C (~500 F) in a shell and tube heat exchanger, and then enter a quench system where the gases are cooled by direct contact with an acrylic acid containing liquid at a temperature less than 120 C (~250 F), preferably less than 110 C (~225 F) and more preferably under 100 C (~212 F). The difference in temperature between the temperature of the bottoms of next distillation column and the temperature of the outlet gases and vapors leaving the quench system is less than 28 C (~50 F), preferably less than 5 C (~10 F) and more preferably less than 3 C (~5 F).

The cooling step can be conducted directly or indirectly in one or more pieces of equipment. For example, the cooling of the gaseous reaction mixture can be initiated in a quench or flash vessel, or can be integrated into the bottom of the dehydration column, with or without column internals. The quench system may contain one or more spray nozzles in one or more locations to distribute the acrylic acid containing quench liquid across the cross sectional area through which the hot gases and vapors must pass. The nozzles may be oriented to spray quench liquid horizontally to the flow path of the hot gases and vapors, or axially in the direction of the flow of the gases and vapors, or against the direction of the flow of the gases and vapors, or any combination of these options. The orientation of the external quench system can be 0-90 degrees relative to the horizontal, preferably 90 degrees or vertical with the hot gases and vapors and quench liquid flowing downwards and co-currently towards the dehydration column inlet. The quench system may also contain one or more trays whose type is not particularly limited or packing or combination of the two. Preferably, the cooling step is initiated or primarily conducted external to the dehydration column.

The acrylic acid containing quench liquid may be comprised of a liquid circulated from the next distillation tower bottoms, combined with one or more acrylic acid containing streams filtered to remove insoluble solids, heated in a heat exchanger to control the temperature, and returned to the quench system. The ratio of the circulated liquid flow rate from the distillation tower bottoms to the combined flow rates of the one or more process streams added to the circulated liquid flow rate from the distillation tower bottoms is 1:1, preferably 5:1 and more preferably 9:1.

In its most simple form, the quench system may be a section of pipe before the pipe enters the dehydration column in which the hot gases and vapors pass through a radial splashing shower of acrylic acid containing liquid accomplished by impinging two opposing axial jets of acrylic acid containing liquid in or near the center of the pipe section. Preferably, a target metal plate with a diameter 0.1 to 0.5 times the internal diameter of the pipe section, preferably 0.2 times the internal diameter of the pipe section, may be located at the center of the two jets and used as an impingement device to create the radial splashing shower of acrylic acid containing quench liquid. Advantageously, a two-phase flow vapor/liquid disengagement device is provided internal to the dehydration column at a point of entrance for the quenched reaction gases and vapor and quench liquid. This device can be of any design that will reduce the velocity of the quenched vapors and gases and quench liquid, separate the majority of the quench liquid from the cooled reaction vapor and gases, and distribute the majority of the cooled reaction vapors and gases across the cross sectional area of the dehydration column. In its simplest form, it is comprised of an impingement baffle located at the inlet of the dehydration column for the quenched reaction vapors and gases and the quench liquid.

One unique feature of the present invention is that the feed to the dehydrator is a two phase feed (i.e. gas and liquid). This is the result of the cooling step. A normal distillation tower has only one phase feed (i.e. a liquid or a gas).

In the process of the invention, the at least partially cooled reaction mixture is dehydrated. The dehydration preferably is conducted in a dehydration column. The dehydration column functions to remove the majority of water from the incoming gaseous reaction mixture. Advantageously, the dehydration column is operated such that there is a bottoms stream and an overhead stream. In a preferred embodiment of the invention, at least a portion of the overhead stream is condensed and is returned as a reflux liquid to the dehydration column.

In one embodiment of the invention, essentially all non-condensibles and lights exit the dehydration column in the overhead stream. Examples of noncondensibles present during the production of acrylic acid include, for example, nitrogen, oxygen, CO, carbon dioxide, and unreacted hydrocarbons such as propane and propylene. Advantageously, the entire overhead stream is introduced into a condenser, and at least a portion of the lights are condensed and returned to the dehydration column as a reflux stream. This condenser can be internal or external to the dehydration column, and it can be of the shell and tube or direct contact type design (e.g., quench cooler). Part of the gas stream from the condenser is recycled to the reactors and the remaining is sent to an incinerator. To further recover acrylic acid as a valuable product, the recycle gas can be sent to a condenser before it is fed to the reactors.

The dehydration column functions, at least partially, as a distillation column. However, as noted above, the dehydration column can also serve as a contacting zone for cooling of the gaseous reaction mixture. Preferably, the pressure in the dehydration column is no higher than the pressure of the incoming gaseous reaction mixture. It is also preferred that the temperature of the bottoms stream from the dehydration column is less than about 120° C. The temperature of the overhead stream from the dehydration column is at least about 40° C.

The vent stream from the overhead condenser on the dehydration column is at least partially recycled to the reactor system. In one embodiment of the invention, a portion of the vent stream is removed from the separation system as a purge stream.

The bottoms stream from the dehydration column advantageously is sent to a second column, except that a portion of this stream can be employed to cool the gaseous reaction mixture. In one embodiment of the invention, a portion of the bottoms stream from the dehydration column is sent to a heat exchanger, which can be a reboiler. However, it is noted that the process can also be operated under conditions such that the heat exchanger is a cooler, depending on whether the process design requires heating or cooling. In a preferred embodiment of the invention, a portion of the bottoms stream from the dehydration column is fed to a second column (also known as a finishing tower). Advantageously, the feed point is the top of the second column. The second column preferably is a distillation column and is used in conjunction with a reboiler and a condenser.

The second column has two product streams, i.e., a side stream and a residue stream. The difference between these streams is the heavy ends content. The two key heavy end components in these streams are the acrylic acid dimer, i.e., Michael addition product, and maleic acid/anhydride. As the take-off ratio of side stream to residue stream increases, these heavy ends concentrate in the residue stream relative to the side stream. The residue stream (sometimes referred to as ester grade acrylic acid) is typically unsuitable as a feed to a melt crystallizer, i.e., a glacial acrylic acid unit, due to the high dimer, inhibitor and maleic acid/anhydride content. This stream, however, can be used as feed for an acrylate ester unit especially if the ester unit is equipped with a dimer cracker. The dimer cracker unit in a butyl acrylate (or other acrylate ester) unit converts most of the dimer back to acrylic acid which is converted into butyl acrylate, i.e., the acrylic content of the dimer is recovered as useable acrylic acid raw material. The maleic acid/anhydride in the residue product reacts with butanol forming esters which are high boilers and easily removed from the butyl acrylate product in the purification train. For esters such as methyl acrylate and ethyl acrylate, the cracking of the dimer can be done in situ by providing sufficient residence time and temperature in the reactor volume in the base of the reaction/esterification tower.

The side stream material which is referred to as technical grade acrylic acid can be fed to a melt crystallizer unit for glacial acrylic acid production or used as feed to any acrylate ester unit. One process enhancement for the finishing tower is to equip its reboiler recirculation loop with a dimer cracker. In this scenario the cracker residue stream is very concentrated and most (>95%) of the acrylic acid product is taken as the side stream product (i.e. technical grade acrylic acid). The highly concentrated residue stream from the cracker can then be incinerated to regain fuel value.

In a preferred embodiment of the invention, the overhead stream from the second column is sent to a condenser. Preferably, the condenser is operated as a "total condenser" in that essentially the entire overhead stream is condensed. However, it is possible to remove a purge stream of noncondensible compounds from this condenser. Advantageously, the condensate from the second column condenser is used to cool the reaction gas mixture, either as is or after additional heat exchange.

The bottoms stream from the second column advantageously is at least partially sent to the second column reboiler. The remainder of the bottoms stream can be incinerated or can be further treated according to known methods; for example, the bottoms stream can be sent to an acrylates ester production unit or can be subjected to a cracking step in which Michael addition compounds are treated to recover acrylic acid, which can then be recycled. In one embodiment of the invention, the bottoms stream contains the majority of the acrylic acid to be recovered from the process. However, in a preferred embodiment of the invention, the majority of acrylic acid is recovered from a side draw stream from the second column.

In view of the fact that the side stream is in the second column, the process of the invention removes product acrylic acid at a point below the point where the reaction gaseous mixture is fed to the separation system, i.e. the product stream is removed below the feed in the separation system.

The temperature and pressure in the second column are not particularly critical, and can be determined according to design considerations well-known to those skilled in the art. Preferably, the second column is operated below the operating pressure of the dehydration column. Preferably, the second column is operated at subatmospheric conditions. This has the advantage of allowing the second column to operate at lower temperatures, thereby minimizing undesired dimer, oligomer and/or polymer formation. Advantageously, the temperature of the overhead stream as it leaves the second column is from about 40 to about 90° C. when producing acrylic acid and operating the second column at a head pressure of from about 40 to about 500 mm Hg. The temperature of the bottoms stream from the second column advantageously is from about 60 to about 120° C. when producing acrylic acid.

Figure 5:
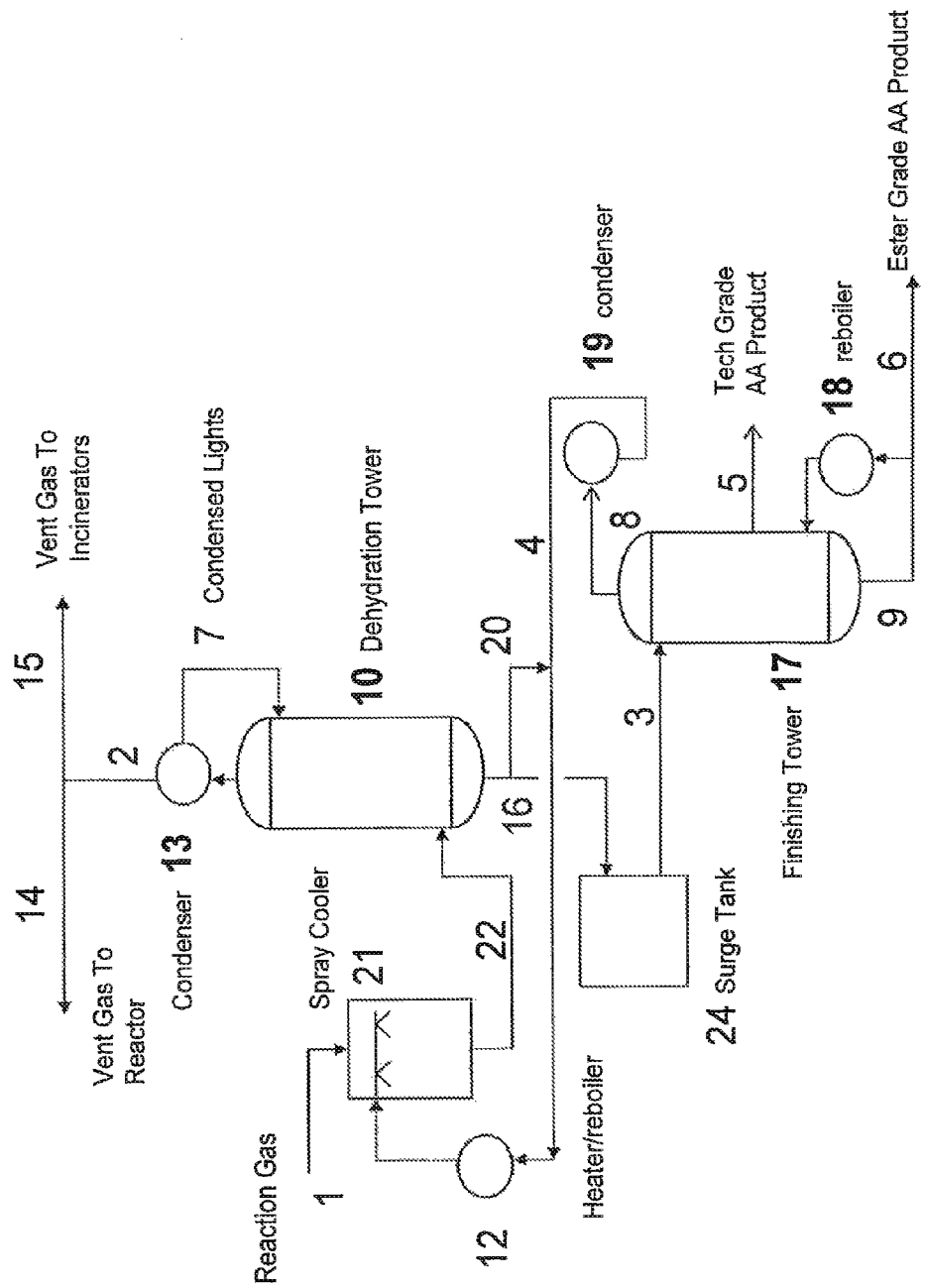
FIG. 5 is a schematic process flow sheet showing a configuration in which at least a portion of the bottoms from the dehydration tower are passed through a surge tank before entering the finishing tower.

The design details of the dehydration column and of the second column, including their operating conditions such as temperatures, pressures, flow rates, equipment sizing including column height and diameters, choice of materials of construction, arrangement and choice of type of auxiliary equipment such as heat exchangers and pumps, choice and arrangement of column internals, and location of piping including take-off streams, can readily be determined by those skilled in the art according to well-known design considerations. Examples of distillation column configurations that can be used in the process of the invention include, for example, packed columns, tray columns, divided wall columns, multi-stage devolatilizers, and the like. Any type of tray can be employed, including bubble trays, valve trays, cross flow trays, dual flow trays, and combinations thereof. Similarly, if packing is employed, any type of packing can be used, including randomly- or regularly-spaced packing. In a preferred embodiment of the invention, the dehydration column comprises packing in its upper section and trays in the lower section. The lower section provides for direct cooling of the incoming gaseous reaction mixture. The number of theoretical stages for the dehydrator and finishing columns are not specifically limited. Preferably 5 to 50 theoretical stages for the dehydrator are used, and more preferably 20 to 30 theoretical stages. Preferably 5 to 30 theoretical stages are used for the finishing column, more preferably 8 to 20 theoretical stages. Surge tanks optionally can be employed within the separation system such as, for example, at one or more locations between the dehydration column and the second column as shown in FIG. 5.

In a preferred embodiment of the invention, the process equipment is at least partially constructed using copper or copper-containing alloys, such as various alloys sold under the mark Monel™. These and other copper-containing alloys provide polymer inhibition for acrylic acid as a result of copper dissolution in the presence of air. Unfortunately, the corrosion rate in the presence of hot streams containing maleic acid is too high for practical commercial use of these alloys in the finishing column. However, the upper section of the dehydrator is essentially free of maleic acid (due to its high boiling point) and this region of the dehydrator can use trays or packing constructed from Monel™ copper-containing alloys as part of a fouling abatement scheme. The use of such packing in this region of the dehydrator provides a self-inhibiting surface which helps alleviate fouling potential due to poor inhibitor distribution in the packing. Other metals, such as stainless steel, including 316 stainless steel, can also be employed as the material(s) of construction for the process equipment by using criteria well known to those skilled in the art.

The use of inhibitors is preferred in the process of the invention, regardless of the choice of materials of construction. Various compounds are well known to inhibit the reaction of acrylic acid, and are commercially available. Examples of preferred inhibitors include soluble manganese ions, soluble copper ions, 2,2,6,6-tetramethyl-1-piperidinyloxy (TEMPO) and related compounds such as 4-hydroxy TEMPO. Combinations of inhibitors can be employed. In a preferred embodiment of the invention, a mixture of a source of soluble manganese ions, such as manganese acetate, and 4-hydroxy TEMPO are employed in the dehydration column as an inhibitor. 4-hydroxy TEMPO/manganese acetate is also the preferred inhibitor for the second column. An alternate inhibitor system that could be used in both columns is hydroquinone/manganese acetate. It is also preferred, as is well-known in the art, to employ molecular oxygen or air to the second column, as oxygen is also known to be an inhibitor. The inhibitor is employed in an amount sufficient to prevent or reduce the polymerization of acrylic acid, as is well known to those skilled in the art. In the case of the current invention, air injection is only required for the second column because the reaction gases fed to the dehydrator already contain oxygen in an amount sufficient for the inhibitor system. Typically, sufficient air is injected such that oxygen is present in the column in an amount of at least 0.1 volume percent relative to the amount of vapor in the column.

One technique frequently used industrially to minimize inhibitor cost is to recycle streams that have a high inhibitor concentration. In the current invention the inhibitor is concentrated in the residue stream of the second column. Accordingly, a portion of this stream can be recycled to either or both the overhead of the dehydrator and/or the overhead of the second column.

Advantageously, an acrylic acid product stream is recovered from the second column as a side draw stream. The location of the side draw on the second column is a matter of design preference, and can be determined using design techniques well-known to those skilled in the art. Preferably, this point of removal is below the feed tray and 2 or 3 theoretical stages above the reboiler. The trays may be of any style design such as cross-flow or dual flow or any combination of the two. This invention also works with packing or any combination of trays and packing. The acrylic acid product is removed from the side of the distillation tower as predominantly a vapor or a liquid. The apparatus for collecting the side stream is comprised of a nozzle and a vapor-liquid separation space where most liquid is separated by gravity from the vapor with or without an internal vapor or liquid collector. The liquid or vapor collector may comprise a pipe with one or more perforations, an inverted funnel, a funnel, a downcomer, a hat tray, an impingement baffle, a liquid distributor, a liquid collector, a baffle or any combination of these. The weight ratio of the side draw to bottom stream is preferably 75:25, or more preferably 95:5. However, advantageously, the side draw to bottom stream weight ratio can also be designed by one skilled in the art to be 25:75 or even 5:95. In a further embodiment, no side draw is taken and all the acrylic acid product is taken in the bottoms stream. As a practical matter, the side stream is typically of better quality than the tails, i.e., the side stream contains less heavy components than does the tails.

One surprising advantage of the process of the invention is that the product stream is produced in high purity by a process that does not require an azeotropic solvent or other solvent. For example, the product stream advantageously contains at least about 98.5% acrylic acid by weight, preferably contains at least about 99% acrylic acid, and more preferably at least about 99.5% acrylic acid. Advantageously the product stream contains less than about 0.5% water and less than about 0.4% acetic acid, preferably contains less than about 0.3% water and less than about 0.2% acetic acid, and more preferably contains less than about 0.15% water and less than about 0.075% acetic acid. The process of the invention preferably can produce a product stream that is usable as technical grade acrylic acid without further separation processing.

One embodiment of the invention is shown in FIG. 1. Referring to FIG. 1, hot reaction gas mixture feed stream 1 containing acrylic acid is introduced into the lower area of dehydration column (or tower) 10. Upon entering the dehydration column, the reaction gas mixture is contacted with, and cooled by, liquid 11 supplied from heat exchanger 12, which can be a cooler or a heater, but preferably is a reboiler. The contacting can comprise spraying, feeding the cooling liquid to a distillation tray or packing through which the hot reaction gaseous mixture rises, or a combination of these. The partially cooled gas mixture flows up the dehydration column through internals (not shown) which can be trays or packing of any configuration, as is well known to those skilled in the art. As the cooled gas mixture flows upward, it is contacted with a reflux liquid comprising condensed lights 7 from condenser 13. Gases and vapors that are not condensed in condenser 13 exit the condenser via condenser overhead stream 2, which is then split into recycle gas stream 14 and vent stream 15. Accordingly, the dehydration column functions to remove the majority of acrylic acid from reaction gas mixture feed stream 1, and to send the recovered acrylic acid via bottoms stream 16 for further treatment.

A portion of bottoms stream 16 from the dehydration tower is fed to a point near the top of second column (or finishing tower) 17 via second column feed stream 3. Another portion of bottoms stream 16 is fed to heat exchanger 12 via heat exchanger feed stream 20 and thus is recirculated to the dehydration column and is employed to cool the incoming hot reaction gas mixture. The liquid from second column feed stream 3 flows downward in the second column where it is contacted with rising vapors from reboiler 18. The second column preferably is a distillation column. The configuration of the distillation column is not particularly critical, and the column can be designed using criteria well known to those skilled in the art. Vapor phase overhead stream 8 from the second column is introduced into condenser 19, where the majority of the overhead stream is condensed. A small purge stream (not shown) of noncondensibles passes out of condenser 19 as a vent stream, which can be disposed of, recycled, or otherwise handled. Condensed liquid from condenser 19 is sent via condensed liquid stream 4 to heat exchanger 12, and then is sent to the dehydration column via cooling liquid stream 11 to cool the gaseous reaction mixture of stream 1. A portion of second column bottoms stream 9 is recirculated to the second column via reboiler 18. The remainder of bottoms stream 9 flows via residual stream 6 for further treatment, disposal, or a combination of these. For example, residual stream 6 can be sent to an esters unit, to a cracking unit, or to a combination of these.

Acrylic acid product stream 5 is taken from the second column as a side draw. The stream preferably is a vapor stream, but can be a liquid stream.

Figure 2:
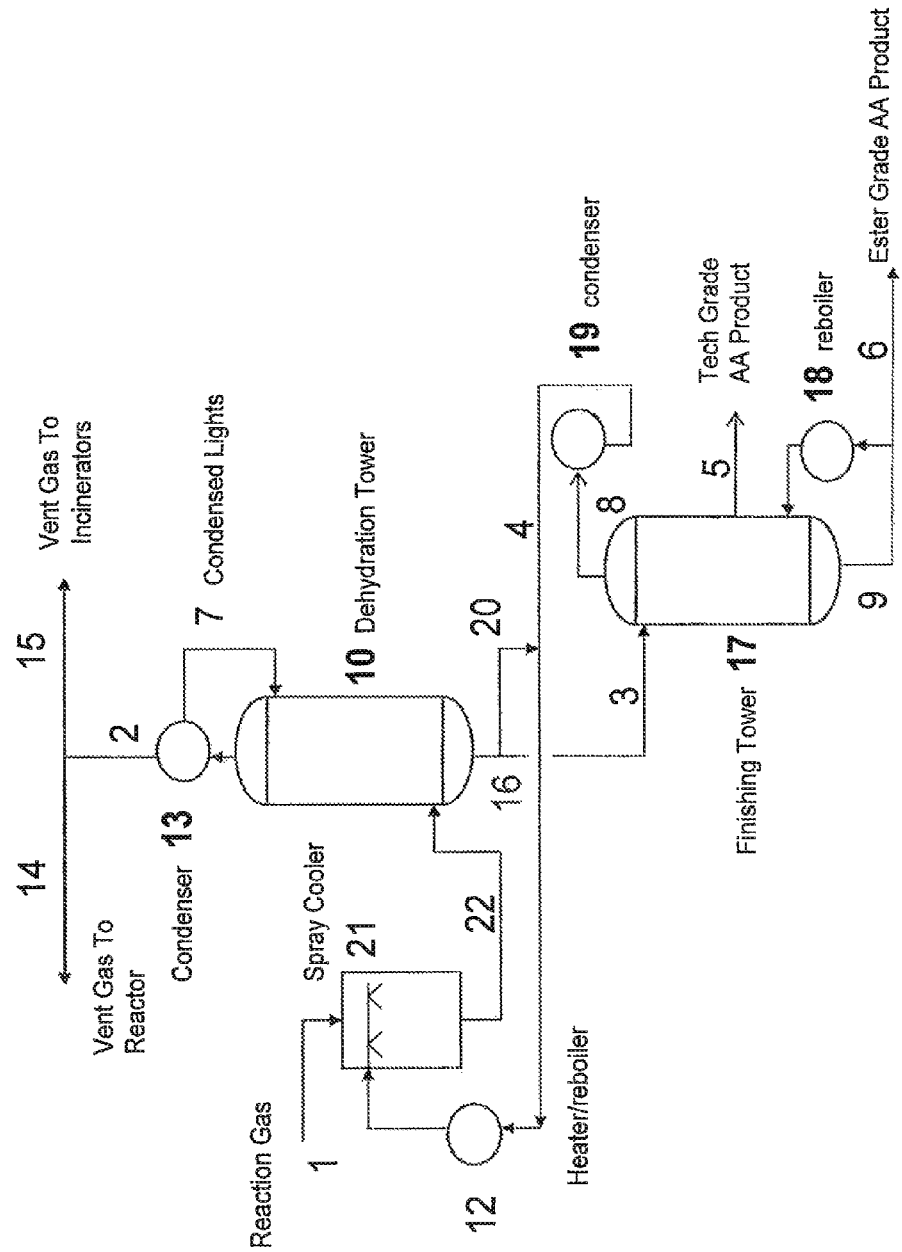
FIG. 2 is a schematic process flow sheet showing a configuration in which cooling of the reaction mixture is conducted primarily in a separate vessel prior to the dehydration column.

FIG. 2 shows a variation of FIG. 1 in which the cooling of gaseous reaction mixture 1 is conducted primarily in a separate vessel prior to the dehydration column. In this embodiment, reaction gas mixture 1 enters spray cooler 21, and cooled reaction gas 22 is removed from the cooler and passed to the dehydration column for processing. In this embodiment, heater/reboiler (heat exchanger) 12 is relocated and fitted within the process scheme so as to receive dehydration column bottoms stream 20, and stream 4 from condenser 19 as feed streams.

Figure 3:
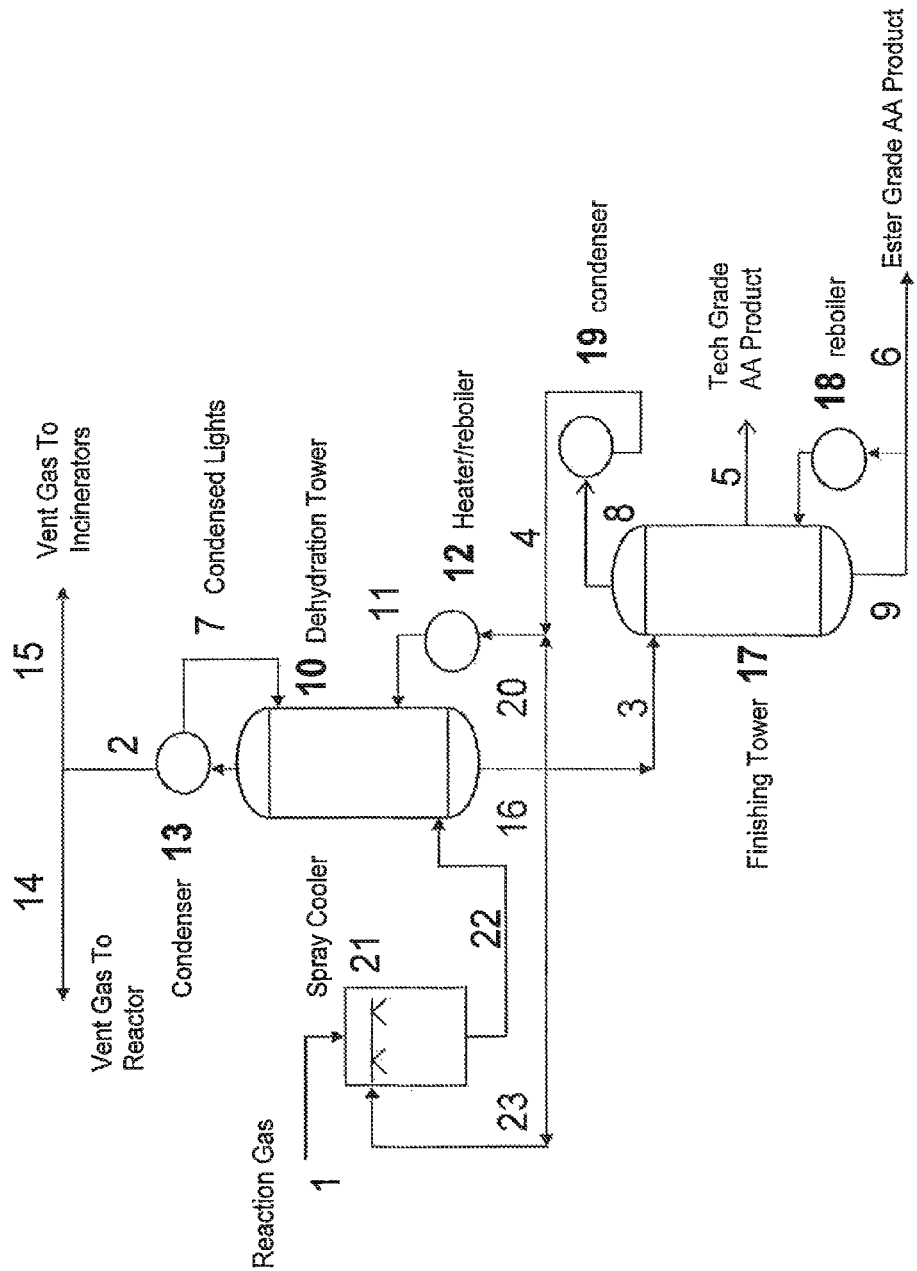
FIGS. 3 and 4 are schematic process flow sheets showing variations of the process shown in FIG. 2.

FIG. 3 shows a variation on FIG. 2 in which heater/reboiler 12 retains the same position that it has in FIG. 1, and the feed streams 23 to spray cooler 21 is now only a portion of dehydration column bottoms stream 16. The size of streams 16, 23, 20 and 4 can vary, usually with the size of stream 23 the largest. In this variation, reaction gas stream 1 is subjected to a stepped cooling process, the first step occurring in spray cooler 21 and the next step in dehydration column 10, i.e., cooled reaction gas stream 22 subjected to further cooling from liquid 11.

Figure 4:
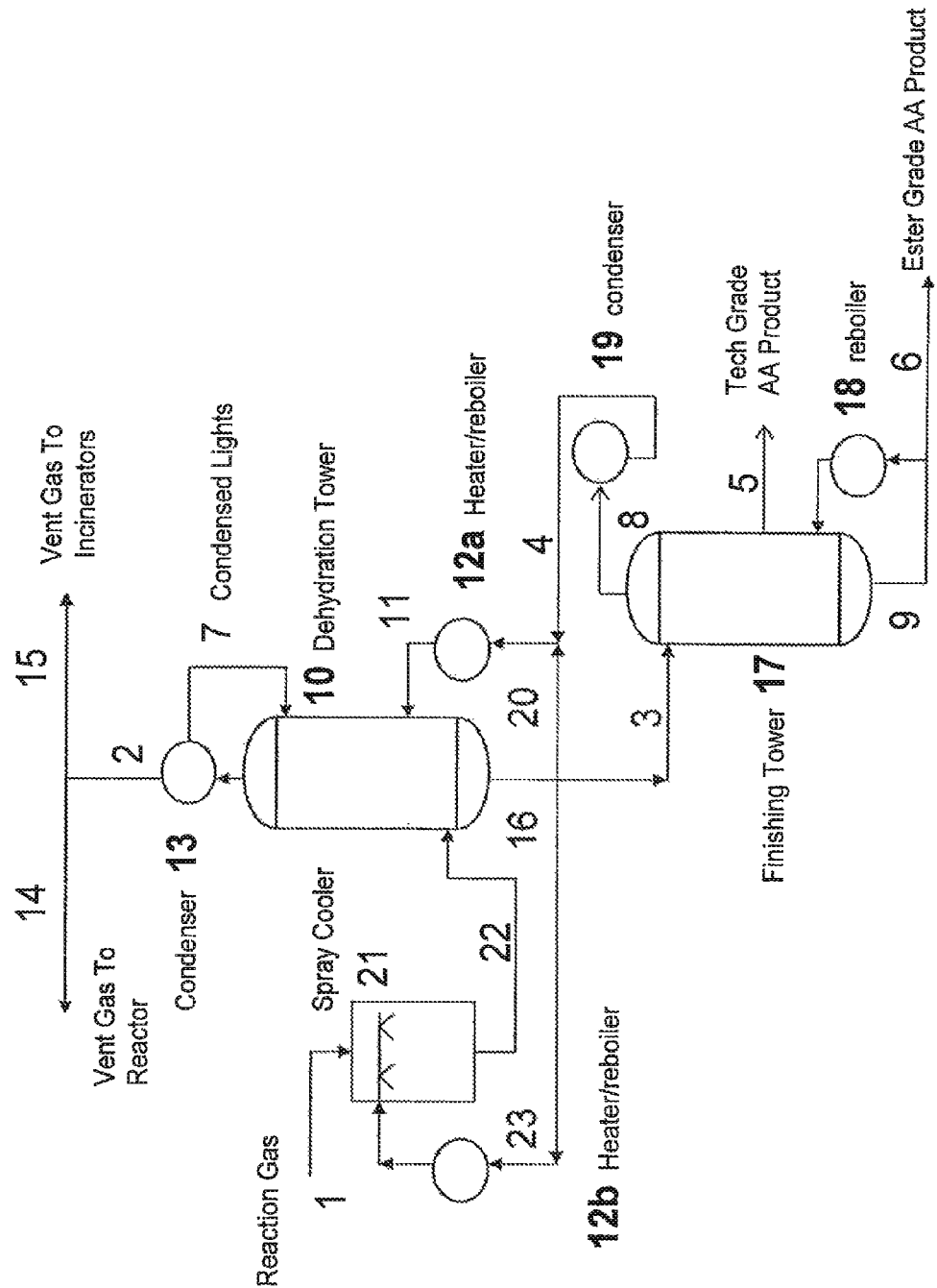

FIG. 4 shows yet another variation on FIG. 2 in which two heater/reboilers are employed, i.e., heater/reboilers 12a and 12b. The heater/reboilers can be the same or different in size and/or design, and heater/reboiler 12a is positioned and connected in essentially the same manner as heater/reboiler 12 in FIG. 1, and heater/reboiler 12b is positioned and connected in essentially the same manner as heater/reboiler 12 in FIG. 2.

FIG. 5 shows still another variation on FIG. 2, and in this instance surge tank 24 is positioned between dehydration tower 10 and finishing tower 17. The position of heater/reboiler 12 relative to spray cooler 21 varies from FIG. 2, but provides essentially the same function, i.e., to at least partially cool the hot reaction gaseous mixture stream 1 before it enters into and is processed within dehydration column 10. Surge tank 24 is positioned such that it can receive a stream of dehydration column bottoms in times of excess flow, and then hold and/or pass these excess bottoms to finishing tower 17 for further processing.

One further embodiment (not shown in FIG. 5) comprises passing at least a portion of the bottoms from the dehydration column through at least one cooler prior to entering the surge tank. Furthermore at least a portion of the stream from the surge tank is passed through at least one pre-heater prior to entering the second column. Advantageously the at least one cooler and the at least one heater can be the same device (i.e., a process-to-process heat exchanger).

SPECIFIC EMBODIMENTS OF THE INVENTION

The following examples are given to illustrate the invention and should not be construed as limiting its scope. All parts and percentages are by weight unless otherwise indicated.

EXAMPLE 1

A separation process is conducted according to the process scheme shown in FIG. 1. A gaseous reaction mixture (3100 g/hr), Stream 1, is introduced into the dehydration column of a separation process. The gaseous reaction mixture contains acrylic acid, which is obtained from the catalytic gas phase oxidation of acrylic acid precursors, and has a temperature of 177° C., a pressure of 18.7 psia, and a composition of 16.6% acrylic acid, 0.9% acetic acid, 6.8% water, 75.2% noncondensibles, and 0.5% other reaction by-products.

The overhead vapor from the dehydration column is partially condensed in a condenser. The vapor stream from the partial condenser (2590 g/hr), Stream 2, has a temperature of 54° C., a pressure of 16.7 psia, and a composition of 0.5% acrylic acid, 1.1% acetic acid, 8.4% water, 89.9% noncondensibles, and 0.1% other reaction by-products. The majority of water in Stream 1 is removed via Stream 2.

The bottoms stream from the dehydration column (1420 g/hr), Stream 3, is sent to a second column. This stream has a temperature of 84° C., a pressure of 16.8 psia, and a composition of 87.4% acrylic acid, 7.4% acetic acid, 4.2% water and 1.0% other impurities.

The overhead stream from the second column is sent to a condenser. The condensate from this condenser (909 g/hr), Stream 4, has a temperature of 60° C., a pressure of 2.9 psia, and a composition of 81.8% acrylic acid, 11.5% acetic acid, 6.6% water and 0.1% other impurities.

The side draw from the second column (516 g/hr), Stream 5, has a temperature of 95° C., a pressure of 3.0 psia, and a composition of about 99.5% acrylic acid and about 0.5% other impurities.

The bottoms stream from the second column (28 g/hr), Stream 6, has a temperature of 110° C., a pressure of 3.0 psia, and a composition of 52.3% acrylic acid, 44.5% heavies, and 3.2% other impurities and polymerization inhibitors.

EXAMPLE 2

Finishing Column Vapor Side Stream Lab Example

A continuous lab distillation column is assembled consisting of a thermo-siphon reboiler equipped with a 1 inch diameter by one foot long section of 0.24 inch stainless steel Pro-Pak™ packing. A vapor side stream apparatus is attached to the top of the packing section. A 20 tray 1 inch Oldershaw section is then placed on top of the vapor side stream apparatus. The top of the column is equipped with a feed section that fed preheated liquid to the top tray of the Oldershaw section via a pump and feed vessel arrangement. An electrically traced total overhead take-off line is attached to the top of the column and this fed vapor directly to a condenser along with an inhibitor solution which is introduced at the top of the condenser. The condenser is connected to a receiver that has been equipped with a vacuum line that connected to a vacuum pump. A pump is used to continually remove liquid from the receiver into a collection vessel. A small air bleed is injected into the reboiler to provide air for the inhibitor. A separate pump is used to remove liquid from the base of the tower through an in-line condenser (for cooling) feeding into a collection vessel. The vapor side stream is sucked from the column into a condenser and receiver via a vacuum line connecting the vapor side stream receiver and the overhead receiver. This line is equipped with a needle valve to control vapor removal rate from the tower. The side stream condenser is continually fed an inhibitor solution and the condensed vapors gravity drained into the side stream receiver. The liquid in the receiver is continually pumped from the receiver into a product vessel. The operating parameters are given in Table 1 for three 30-minute mass balance run's.

TABLE 1

| Operating Parameters | | | |
| --- | --- | --- | --- |
| Run | 1 | 2 | 3 |
| Feed to top of tower (g) | 289 | 288 | 289 |
| Overhead product (g) | 222 | 222 | 222 |
| Vapor side stream product (g) | 58 | 58 | 57 |

TABLE 1-continued

Operating Parameters

| Run | 1 | 2 | 3 |
|---|---|---|---|
| Residue product (g) | 18 | 18 | 19 |
| Feed temperature (C.) | 73 | 73 | 76 |
| Overhead vapor temperature (C.) | 74 | 75 | 78 |
| Reboiler temperature (C.) | 92 | 92 | 93 |
| Overhead pressure (torr) | 110 | 110 | 110 |
| Air injection into reboiler (cc/min) | 10.2 | 10.2 | 10.2 |
| Side stream inhibitor flow (mL/min)* | 0.2 | 0.2 | 0.2 |
| Overhead receiver inhibitor flow (mL/min)** | 0.1 | 0.1 | 0.1 |

*Inhibitor solution = 1% PTZ in acrylic acid.
**Inhibitor solution = 1% 4-hydroxy TEMPO and 0.1% Mn(OAc)$_4$ in acrylic acid.

The stream and product compositions for the three mass balance runs are shown in Tables 2A-D.

TABLE 2A

Feed Stream Compositions

| Run | 1 | 2 | 3 |
|---|---|---|---|
| % Acrylic acid | 86.9 | 86.9 | 93.8 |
| % Acetic acid | 8.9 | 8.8 | 2.8 |
| % Water | 4 | 4.1 | 3.2 |
| % Maleic acid | 0.22 | 0.24 | 0.17 |
| % Formaldehyde | — | — | 0.22 |
| % Furfural | — | 0.015 | 0.013 |
| % Benzaldehyde | — | 0.025 | 0.022 |
| ppm TEMPO | 300 | 400 | 300 |
| ppm Mn(II) | 6 | 8 | 6 |

TABLE 2B

Overhead Product Compositions

| Run | 1 | 2 | 3 |
|---|---|---|---|
| % Acrylic acid | 82.8 | 84.2 | 91.7 |
| % Acetic acid | 11.8 | 11 | 4 |
| % Water | 4 | 4.1 | 4.3 |
| Maleic acid | 0.0007 | 0.001 | 0.0009 |
| % Formaldehyde | — | — | 0.33 |
| % Furfural | — | 0.008 | 0.008 |
| % Benzaldehyde | — | 0.008 | 0.007 |

TABLE 2C

Vapor Side Stream Compositions

| Run | 1 | 2 | 3 |
|---|---|---|---|
| % Acrylic acid | 99.8 | 99.8 | 99.9 |
| % Acetic acid | 0.033 | 0.037 | 0.028 |
| % Water | 0.1 | 0.1 | 0.045 |
| % Maleic acid | 0.0062 | 0.0085 | 0.0057 |
| Formaldehyde | — | — | 0.001 |
| % Furfural | — | 0.01 | 0.009 |
| Benzaldehyde | — | 0.008 | 0.008 |

TABLE 2D

Residue Product Compositions

| Run | 1 | 2 | 3 |
|---|---|---|---|
| % Acrylic Acid | 91.6 | 92.6 | 86.2 |
| % Acetic acid | 0.012 | 0.095 | 0.081 |
| % Water | 0.011 | 0.013 | 0.009 |
| % Maleic acid | 1.48 | 1.97 | 0.82 |

EXAMPLE 3

Finishing Column Liquid Side Stream

An Oldershaw column similar to the one used Example 2 is assembled, but the packed column section is replaced with a 5 tray 1 inch Oldershaw section and the vapor side stream section is replaced with a liquid side stream section which does not have inhibitor injection. The operating parameters for three 30-minute mass balance runs are reported in Table 3A.

TABLE 3A

Finishing Column Operating Parameters

| Run | 4 | 5 | 6 |
|---|---|---|---|
| Feed to top of tower (g) | 325 | 324 | 324 |
| Overhead product (g) | 247 | 246 | 248 |
| Liquid side stream product (g) | 57 | 57 | 57 |
| Residue product (g) | 21 | 21 | 21 |
| Feed temperature (C.) | 70 | 68 | 68 |
| Overhead vapor temperature (C.) | 74 | 72 | 71 |
| Reboiler temperature (C.) | 98 | 98 | 98 |
| Overhead pressure (torr) | 110 | 110 | 110 |
| Air injection into reboiler (cc/min) | 10.2 | 10.2 | 10.2 |
| Overhead receiver inhibitor flow (mL/min)* | 0.1 | 0.1 | 0.1 |

*The inhibitor solution is 1% 4-hydroxy-TEMPO and 0.1% Mn(OAc)4 in acrylic acid.

The stream compositions for the three 30-minute mass balance runs are shown in Tables 3B-E.

TABLE 3B

Feed Stream Compositions

| Run | 4 | 5 | 6 |
|---|---|---|---|
| % Acrylic acid | 78.5 | 80.8 | 78.9 |
| Acetic acid | 15.5 | 14.1 | 14.7 |
| % Water | 5.9 | 4.9 | 6.2 |
| % Maleic acid | | 0.6 | 0.6 |
| Formaldehyde | | 0.14 | 0.16 |
| ppm TEMPO | 400 | 400 | 400 |
| ppm Mn(II) | 8 | 8 | 8 |

TABLE 3C

Overhead Stream Compositions

| Run | 4 | 5 | 6 |
|---|---|---|---|
| % Acrylic acid | 73.8 | 73.7 | 76.6 |
| % Acetic acid | 19 | 18.8 | 16.2 |
| % Water | 7.2 | 7.3 | 7.1 |
| % Maleic acid | — | 0 | 0 |
| % Formaldehyde | 0.18 | 0.07 | |

TABLE 3D

Liquid Side Stream Compositions

| Run | 4 | 5 | 6 |
|---|---|---|---|
| % Acrylic acid | 99.9 | 99.9 | 99.9 |
| % Acetic acid | 0.05 | 0.08 | 0.04 |
| % Water | 0.01 | 0.004 | 0.003 |
| % Maleic acid | — | 0.05 | 0.05 |
| % Formaldehyde | — | 0.002 | 0.002 |

TABLE 3E

Residue Stream Compositions

| Run | 4 | 5 | 6 |
|---|---|---|---|
| % Acrylic Acid | 79.5 | 81.6 | 83.6 |
| % Acetic acid | 0.03 | 0.02 | 0.03 |
| % Water | 0.01 | 0.004 | 0.005 |
| % Maleic acid | — | 0.5 | 0.52 |

EXAMPLE 4

Dehydrator

A laboratory-scale dehydrator is assembled by placing a feed section on top of a reboiler. A 1-inch packed section containing 0.24 inch stainless steel Pro-Pak™ is then placed on top of the feed section and the packed section is topped with another feed section which allows recirculation of the reboiler contents to the top of the packed section along with a liquid feed to the column. The feed section on the reboiler is fed vapor from a tube furnace in which simulated reactor liquid feed, air and nitrogen are introduced. The tube furnace vaporizes the liquid and heats the gases to simulate a hot acrylic acid reactor feed. The feed section on top of the packing section is topped with 25 1-inch Oldershaw trays. On top of the trays is placed a feed section for returning preheated reflux to the column. The reflux section is topped with an electrically heated total take-off which led to a warm partial condenser and receiver equipped with an inhibitor feed. The liquid from the partial condenser is fed to the top of the column as reflux. The partially condensed vapor and inerts are then fed to a cold condenser and receiver which condenses out the remaining vapor allowing the inerts to be purged through the vent. The cold liquid is continually pumped out of the column as overhead product into an overhead product vessel. A liquid product is also continually pumped from the reboiler through a condenser into a residue product vessel. The operating parameters for three 30-minute mass balance runs are reported in Table 4A.

TABLE 4A

Operating Parameters

| Run | 7 | 8 | 9 |
|---|---|---|---|
| Vaporizer feed (g) | 117 | 118 | 118 |
| Feed to top of packing (g) | 248 | 249 | 249 |
| Overhead product (g) | 34 | 34 | 34 |
| Residue product (g) | 324 | 325 | 325 |
| Reboiler recirculation rate (mL/min) | 8.2 | 8.2 | 4.1 |
| Inhibitor feed rate (mL/min)* | 0.1 | 0.1 | 0.1 |
| Nitrogen feed rate to vaporizer (L/min) | 8.75 | 8.75 | 8.75 |
| Air feed rate to vaporizer (L/min) | 1.56 | 1.56 | 1.56 |
| Vapor feed to column T (C.) | 176 | 176 | 175 |
| Temp of feed to packing (C.) | 106 | 106 | 96 |
| Reboiler Temp (C.) | 87 | 88 | 89 |
| Overhead Temp (C.) | 66 | 66 | 65 |
| Partial condenser Temp (C.) | 52 | 52 | 53 |
| Reflux Temp (C.) | 52 | 52 | 53 |
| Reflux flow rate (mL/min) | 1.7 | 1.7 | 1.6 |

*The inhibitor is 1% 4-hydroxy-TEMPO and 0.1% Mn(OAc)2 in a water solution.

The stream compositions for the three 30-minute mass balance runs are reported in Tables 4B-E.

TABLE 4B

Feed Stream Compositions

| Run | 7 | 8 | 9 |
|---|---|---|---|
| % Acrylic acid | 67.7 | 68.2 | 67.4 |
| % Acetic acid | 4 | 3.9 | 4.3 |
| % Water | 26.7 | 26.4 | 26.8 |
| ppm 4-hydroxy TEMPO | 400 | 400 | 400 |
| ppm Mn(II) | 8 | 8 | 8 |

TABLE 4C

Feed Stream to Top of Packing Compositions

| Run | 7 | 8 | 9 |
|---|---|---|---|
| % Acrylic acid | 71.6 | 72.5 | 72.6 |
| % Acetic acid | 22.1 | 21.3 | 21.4 |
| % Water | 6.3 | 6.2 | 6 |
| ppm 4-hydroxy TEMPO | 200 | 200 | 200 |
| ppm Mn(II) | 8 | 8 | 8 |

TABLE 4D

Overhead Stream Compositions

| Run | 7 | 8 | 9 |
|---|---|---|---|
| % Acrylic acid | 5.3 | 5.7 | 5 |
| % Acetic acid | 13 | 14.1 | 14.8 |
| % Water | 81.7 | 80.2 | 79.5 |

TABLE 4E

Residue Stream Compositions

| Run | 7 | 8 | 9 |
|---|---|---|---|
| % Acrylic acid | 78.7 | 77.8 | 78.9 |
| % Acetic acid | 16.3 | 16.6 | 15.9 |
| % Water | 5 | 5.6 | 5.2 |

EXAMPLE 5

Dehydrator and Finishing Columns Coupled

The laboratory-scale dehydrator column and the laboratory-scale liquid side stream finishing column described above are coupled by taking the residue product stream from the dehydrator column and feeding it to the top of the finishing column and taking the finishing column overhead product stream and feeding it to the top of the packed section of the dehydrator column. In runs 10 and 11 a 2 hour surge vessel is used between the two columns and for run 12 no surge vessel is used (i.e. the streams fed directly from one column into the other column). The operating parameters for three 30-minute mass balance runs are reported in Table 5A.

TABLE 5A

Operating Parameters

| Run | 10 | 11 | 12 |
|---|---|---|---|
| Dehydrator Vaporizer feed (g) | 118 | 118 | 117 |
| Dehydrator Feed to top of packing (g) | 248 | 249 | 247 |
| Dehydrator Overhead product (g) | 34 | 34 | 34 |
| Dehydrator Residue product (g) | 325 | 325 | 325 |
| Dehydrator Reboiler recirculation rate (mL/min) | 8.2 | 8.2 | 4.1 |
| Dehydrator Inhibitor feed rate (mL/min)* | 0.1 | 0.1 | 0.1 |
| Dehydrator Nitrogen feed rate to vaporizer (L/min) | 8.75 | 8.75 | 8.75 |
| Dehydrator Air feed rate to vaporizer (/min) | 1.56 | 1.56 | 1.56 |
| Dehydrator Vapor feed to column Temp (C.) | 175 | 176 | 174 |
| Dehydrator Temp of feed to packing (C.) | 105 | 107 | 105 |
| Dehydrator Reboiler Temp (C.) | 84 | 90 | 90 |
| Dehydrator Overhead Temp (C.) | 65 | 65 | 65 |
| Dehydrator Partial condenser Temp (C.) | 51 | 52 | 50.5 |
| Dehydrator Reflux Temp (C.) | 51 | 52 | 62 |
| Dehydrator Reflux flow rate (mL/min) | 1.7 | 1.7 | 1.8 |
| Finishing Feed to top of tower (g) | 324 | 324 | 325 |
| Finishing Overhead product (g) | 246 | 248 | 247 |
| Finishing Liquid side stream product (g) | 57 | 57 | 57 |
| Finishing Residue product (g) | 21 | 21 | 21 |
| Finishing Feed temperature (C.) | 68 | 68 | 68 |
| Finishing Overhead vapor temperature (C.) | 72 | 71 | 71 |
| Finishing Reboiler temperature (C.) | 98 | 98 | 94 |
| Finishing Overhead pressure (torr) | 110 | 110 | 110 |
| Finishing Air injection into reboiler (cc/min) | 10.2 | 10.2 | 10.2 |
| Finishing Overhead receiver inhibitor (mL/min)** | 0.1 | 0.1 | |

*The inhibitor is 2% 4-hydroxy-TEMPO and 0.2% Mn(OAc)2 in a water solution.
**The inhibitor solution is 2% 4-hydroxy-TEMPO and 0.2% Mn(OAc)4 in acrylic acid.

The stream and product compositions for the three 30-minute mass balance runs are reported in Tables 5B-I.

TABLE 5B

Compositions of Dehydrator Feed Stream to Vaporizer

| Run | 10 | 11 | 12 |
|---|---|---|---|
| % Acrylic acid | 67.7 | 67.6 | 67.6 |
| % Acetic acid | 3.9 | 4.4 | 4.3 |
| % Water | 26.9 | 26.6 | 26.6 |
| % Maleic acid | 0.54 | 0.49 | 0.46 |
| % Formaldehyde | 1.02 | 0.9 | 0.97 |
| ppm 4-hydroxy TEMPO | 400 | 400 | 400 |
| ppm Mn(II) | 8 | 8 | 8 |

TABLE 5C

Compositions of Dehydrator Feed Stream to Top of Packing

| Run | 10 | 11 | 12 |
|---|---|---|---|
| % Acrylic acid | 74.8 | 75.1 | 69.8 |
| % Acetic acid | 18.2 | 17.2 | 21.6 |
| % Water | 6.8 | 7.5 | 8.4 |
| % Maleic acid | 0.02 | 0.001 | 0 |
| % Fromaldehyde | 0.18 | 0.19 | 0.19 |
| ppm 4-hydroxy TEMPO | ~200 | ~200 | ~200 |
| ppm Mn(II) | ~4 | ~4 | ~4 |

TABLE 5D

Dehydrator Overhead Product Compositions

| Run | 10 | 11 | 12 |
|---|---|---|---|
| % Acrylic acid | 6.2 | 6.5 | 5.7 |
| % Acetic acid | 10.1 | 8.6 | 9.9 |
| % Water | 82.9 | 84.5 | 84.2 |
| % Maleic acid | 0 | 0 | 0 |
| % Fromaldehyde | 0.75 | 0.37 | 0.83 |

TABLE 5E

Dehydrator Residue Product Compositions

| Run | 10 | 11 | 12 |
|---|---|---|---|
| % Acrylic acid | 78.7 | 79.7 | 77 |
| % Acetic acid | 14.8 | 14.2 | 15.8 |
| % Water | 6.3 | 5.9 | 6.3 |
| % Maleic acid | 0.07 | 0.07 | 0.06 |
| % Formaldehyde | 0.15 | 0.17 | 0.15 |
| ppm 4-hydroxy TEMPO | ~400 | ~400 | ~400 |
| ppm Mn(II) | ~8 | ~8 | ~8 |

TABLE 5F

Finishing Feed Compositions

| Run | 10 | 11 | 12 |
|---|---|---|---|
| % Acrylic acid | 80.8 | 78.9 | 77% |
| Acetic acid | 14.1 | 14.7 | 15.8 |
| % Water | 4.9 | 6.2 | 6.3 |
| % Maleic acid | 0.06 | 0.06 | 0.06 |
| % Formaldehyde | 0.14 | 0.16 | 0.15 |
| ppm 4-hydroxy TEMPO | ~400 | ~400 | ~400 |
| ppm Mn(II) | ~8 | ~8 | ~8 |

TABLE 5G

Finishing Overhead Product Compositions

| Run | 10 | 11 | 12 |
|---|---|---|---|
| % Acrylic acid | 73.7 | 76.6 | 69.8 |
| % Acetic acid | 18.8 | 16.2 | 21.6 |
| % Water | 7.3 | 7.1 | 8.4 |
| % Maleic acid | 0 | 0 | 0 |
| % Formaldehyde | 0.18 | 0.07 | 0.19 |
| ppm 4-hydroxy TEMPO | ~200 | ~200 | ~200 |
| ppm Mn(II) | ~4 | ~4 | ~4 |

TABLE 5H

Finishing Liquid Side Stream Compositions

| Run | 10 | 11 | 12 |
|---|---|---|---|
| % Acrylic acid | 99.9 | 99.9 | 99.9 |
| % Acetic acid | 0.08 | 0.04 | 0.09 |
| % Water | 0.004 | 0.003 | 0.006 |
| % Maleic acid | 0.05 | 0.05 | 0.06 |
| % Formaldehyde | 0.002 | 0.002 | 0.002 |
| ppm 4-hydroxy TEMPO | ~300 | ~300 | ~300 |
| ppm Mn(II) | ~6 | ~6 | ~6 |

TABLE 5I

Finishing Residue Product Compositions

| Run | 10 | 11 | 12 |
|---|---|---|---|
| % Acrylic Acid | 81.6 | 83.6 | 86.8 |
| % Acetic acid | 0.02 | 0.03 | 0.02 |
| % Water | 0.004 | 0.005 | 0.006 |
| % Maleic acid | 0.5 | 0.52 | 0.28 |
| % Formaldehyde | 0.004 | 0.005 | 0.004 |
| ppm 4-hydroxy TEMPO | ~2500 | ~2500 | ~2500 |
| ppm Mn(II) | ~50 | ~50 | ~50 |

Although the invention is described above in considerable detail, this detail is for the purpose of illustration. Many variations and modifications can be made on the invention without departing from its spirit and scope as described in the following claims. All publications identified above, specifically including all U.S. patents, allowed patent applications, and published U.S. patent applications, are incorporated in their entirety herein by reference.

What is claimed is:

1. A process for the recovery of (meth)acrylic acid without the use of azeotropic solvent, the process comprising:
    A. Cooling a gaseous reaction mixture comprising (meth) acrylic acid, the mixture obtained from the gas-phase oxidation of at least one (meth)acrylic acid precursor;
    B. Dehydrating the cooled gas mixture in a dehydration column to produce a dehydration column overhead stream and a dehydration column bottoms stream wherein the dehydrating is carried out without using a solvent that forms an azeotrope with water;
    C. At least partially condensing the dehydration column overhead stream to form a condensate, and returning at least a portion of the condensate to the dehydration column as reflux;
    D. Dividing the dehydration column bottoms stream into at least first and second dehydration column bottom streams, and passing at least a portion of one of the first and second dehydration column bottoms stream to a dehydration column heater/reboiler and passing at least a portion of the other dehydration column bottoms stream to the upper half of a second column;
    E. Subjecting the portion of the bottoms stream passed to the second column to distillation within the second column to produce at least a second column overhead stream and a second column bottoms stream comprising heavy components;
    F. At least partially condensing the second column overhead stream to form a second overhead condensate, and passing at least a portion of the second overhead condensate to the dehydration column heater/reboiler; and
    G. Passing at least a portion of the second column bottoms stream to a second column heater/reboiler, and
    H. Providing one or more inhibitor solutions to one or more locations in the process, said inhibitor solutions comprising
        (i) one or more inhibitors selected from the group consisting of hydroquinone; phenothiazine (PTZ); soluble manganese ions; soluble copper ions; 2,2,6,6-tetramethyl-1-piperidinyloxy (TEMPO); 4-hydroxy TEMPO; and manganese acetate, and
        (ii) one or more liquid stream carriers consisting essentially of water, or acrylic acid, or mixtures of water and acrylic acid.

2. The process of claim 1 wherein the one or more locations includes the dehydration column overhead condensate.

3. The process of claim 1 wherein at least one of the one or more inhibitor solutions comprises hydroquinone and water.

4. The process of claim 3 wherein the inhibitor solution further comprises manganese acetate.

5. The process of claim 1 wherein the inhibitor solution comprises water, at least 1% 4-hydroxy TEMPO, and at least 0.1% manganese acetate, by weight.

6. The process of claim 1 wherein the one or more locations within the process includes the second overhead condensate.

7. The process of claim 6 wherein at least one of the one or more inhibitor solutions comprises 4-hydroxy TEMPO and manganese acetate.

8. The process of claim 6 wherein at least one of the one or more inhibitor solutions comprises acrylic acid, at least 1% 4-hydroxy TEMPO, and at least 0.1% manganese acetate, by weight.

9. The process of claim 1 wherein at least one of the one or more inhibitor solutions comprises acrylic acid, hydroquinone, and PTZ.

10. The process of claim 1 further comprising:
    (a) recovering a liquid side draw product stream from the second column, and
    (b) providing an inhibitor solution comprising PTZ and acrylic acid to the liquid side draw product stream.

11. The process of claim 1 further comprising:
    (a) recovering a vapor side draw product stream from the second column,
    (b) condensing said vapor side draw product stream in a side stream condenser to recover a liquid side draw product stream, and
    (c) continuously feeding an inhibitor solution comprising PTZ and acrylic acid to said side stream condenser.

12. The process of claim 11 wherein the inhibitor solution further comprises hydroquinone.

13. The process of claim 1 wherein gas comprising molecular oxygen is provided to one or more locations.

14. The process of claim 1 wherein air is injected into the reboiler of the second column whereby oxygen is present in the second column in an amount of at least 0.1 volume percent relative to the amount of vapor in the second column.

15. The process of claim 1 in which the at least a portion of the other dehydration column bottoms stream passes to the top of the second column.

16. The process of claim 1 wherein at least a portion of the second column bottoms stream recycles to the overhead of the dehydration column, the overhead of the second column, or both.

17. The process of claim 1 wherein the second column bottoms stream comprises 4-hydroxy TEMPO, manganese, or both, and has a temperature from about 60 to about 120 degrees C.

18. The process of claim 13 wherein at least a portion of the second column bottoms stream is sent to a butyl acrylate production unit.

19. The process of claim 13 wherein at least a portion of the second column bottoms stream is sent to an acrylates ester production unit equipped with a dimer cracker.

20. The process of claim 13 wherein at least a portion of the second column bottoms stream is subjected to a cracking step in which Michael addition compounds are treated to recover acrylic acid.

* * * * *